United States Patent
Brimhall et al.

(10) Patent No.: US 6,801,629 B2
(45) Date of Patent: Oct. 5, 2004

(54) PROTECTIVE HEARING DEVICES WITH MULTI-BAND AUTOMATIC AMPLITUDE CONTROL AND ACTIVE NOISE ATTENUATION

(75) Inventors: Owen D. Brimhall, South Jordan, UT (US); Craig M. Collotzi, Sandy, UT (US); Gregory N. Koskowich, Salt Lake City, UT (US)

(73) Assignee: Sonic Innovations, Inc., Salt Lake City, UT (US)

( * ) Notice: Subject to any disclaimer, the term of this patent is extended or adjusted under 35 U.S.C. 154(b) by 556 days.

(21) Appl. No.: 09/745,753

(22) Filed: Dec. 22, 2000

(65) Prior Publication Data

US 2002/0080979 A1 Jun. 27, 2002

(51) Int. Cl.[7] .................................................. A61E 4/06
(52) U.S. Cl. ........................ 381/72; 381/94.1; 381/94.3
(58) Field of Search ........................ 381/72, 94.1, 94.3, 381/56, 57, 309, 26

(56) References Cited

U.S. PATENT DOCUMENTS

| | | | |
|---|---|---|---|
| 3,098,121 A | * | 7/1963 | Wadsworth .................. 381/72 |
| 3,890,474 A | | 6/1975 | Glicksberg .............. 179/107 E |
| 4,880,076 A | | 11/1989 | Ahlberg et al. ............. 181/130 |
| 4,985,925 A | | 1/1991 | Langberg et al. ............. 381/72 |
| 5,002,151 A | | 3/1991 | Oliveira et al. ............. 181/130 |
| 5,031,219 A | | 7/1991 | Ward et al. ................ 381/68.6 |
| 5,201,007 A | | 4/1993 | Ward et al. ................ 381/68.6 |
| 5,305,387 A | | 4/1994 | Sapiejewski ................. 381/71 |
| 5,355,418 A | | 10/1994 | Kelsey et al. ................ 381/72 |
| 5,550,923 A | * | 8/1996 | Hotvet ........................ 381/72 |
| 5,600,729 A | | 2/1997 | Darlington et al. ........... 381/71 |
| 5,740,258 A | | 4/1998 | Goodwin-Johansson ..... 381/72 |
| 5,920,636 A | | 7/1999 | Oliveira et al. ............. 381/328 |
| 5,996,584 A | | 12/1999 | Oliveira et al. ............. 128/864 |

FOREIGN PATENT DOCUMENTS

| | | | | |
|---|---|---|---|---|
| JP | 401017596 A | * | 1/1989 | ............ H04R/3/00 |
| JP | 403214999 A | * | 9/1991 | ............ H04R/1/10 |

* cited by examiner

*Primary Examiner*—Melur Ramakrishnaiah
(74) *Attorney, Agent, or Firm*—Thelen Reid & Priest LLP; David B. Ritchie

(57) ABSTRACT

A noise attenuating system includes a core portion adapted to actively filter sound waves into various bands, passing only those bands corresponding to safe amplitude sounds to a wearer's ear canal. Unlike conventional active noise cancellation systems, active noise attenuation is accomplished without providing additional sound waves inverse to unsafe amplitude sound waves. Instead, unsafe amplitude sound waves are passively blocked, and only safe amplitude sound waves are passed through to the wearer's ear canal.

17 Claims, 9 Drawing Sheets

FIG. 10  FIG. 10A

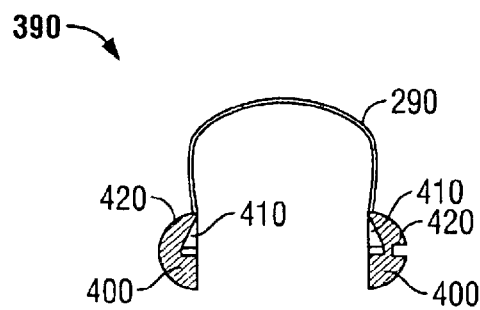 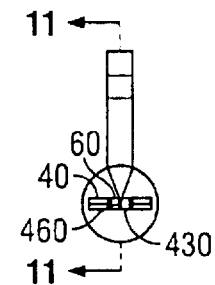
FIG. 11  FIG. 11A
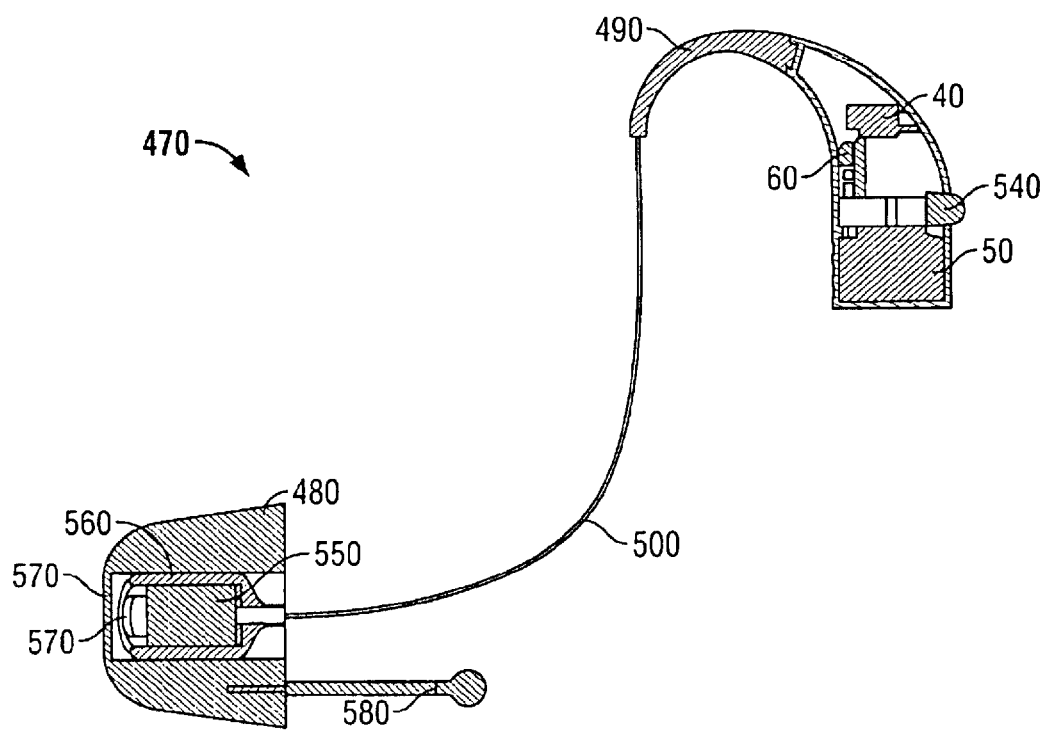
FIG. 12

PROTECTIVE HEARING DEVICES WITH MULTI-BAND AUTOMATIC AMPLITUDE CONTROL AND ACTIVE NOISE ATTENUATION

BACKGROUND OF THE INVENTION

1. Field of the Invention

This invention relates generally to protective hearing devices and, more particularly, to protective hearing devices with active sound attenuation and control.

2. Background

Environmental sounds typically comprise a mixture of various sound wave frequencies having varying intensities. It is well documented that repeated or prolonged exposure to sound waves of certain frequencies and intensities can damage the auditory organ and cause serious hearing problems, including deafness. Injurious noises, such as those caused by explosions or bursts, are often comprised of a mixture of sound wave frequencies of varying intensity. These dangerous sound waves are in both the high and low frequency bands and have an intensity sufficient to cause hearing damage. Individuals who are frequently exposed to sound waves at dangerous frequencies and/or intensities run the risk of incurring permanent injuries, such as hearing loss or even deafness. Such individuals include workers at demolition or construction sites, operators of heavy, noisy equipment and those in active military service. These individuals need hearing protection to prevent losses in hearing acuity and/or gradual increases in hearing thresholds resulting from extended exposures to loud noises.

Passive sound attenuation devices which specifically address this problem are well known. These include conventional earplugs, earmuffs and the like, which function to reduce the negative effects of exposure to dangerous sound frequencies and intensities by limiting the entry of all sound waves into the auditory organ. These conventional devices suffer from a significant disadvantage, however; namely, that auditory access to environmental sounds of relatively risk free frequencies and intensities is also limited. In particular, these devices typically provide much greater attenuation at high frequencies than at low frequencies, as well as excessive attenuation at high frequencies. The result is that wearers of these devices who want or need to hear non-dangerous sounds are prevented from doing so. Therefore, while these devices may be protective against the effects of overexposure to sound having dangerous frequencies and intensities, they create a new danger in that they shut out all environmental sounds, including non-dangerous speech and warning sounds.

Active noise cancellation has been another approach to noise reduction. Active noise cancellation systems eliminate unwanted sound using destructive interference. Cancellation is achieved by propagating "anti-noise," identical to the unwanted sound waves, but inverted. The anti-noise waves interact with the unwanted noise wave resulting in cancellation. A feedback active cancellation headset typically includes a sound generator in each earpiece for producing anti-noise, and a residual microphone, also located in each earpiece, to provide feedback signals to a controller that generates the anti-noise signals. Each microphone detects the unwanted noise within each earpiece and provides corresponding signals to the controller. The controller supplies anti-noise signals to the sound generator corresponding to the noise detected in the earpieces, but inverted, with respect to the unwanted waveform. When the anti-noise interacts with the noise within each earpiece, destructive interference between the noise and the anti-noise cancels the unwanted sound.

For example, U.S. Pat. No. 5,600,729 to Darlington et al. discloses a device comprising a microphone located upstream of a loudspeaker relative to the approaching direction of unwanted noise waves, in an assembly adapted to be mounted at a site of entry of the noise into the ear chamber. The output of the microphone is amplified and fed to the downstream loudspeaker to produce noise that tends to cancel the unwanted intrusive noise. The device is attached by means of a headband.

U.S. Pat. No. 3,890,474 to Glicksberg discusses the incorporation of sound amplitude limiting into a device that is self-contained in the ear canal of the wearer. The sound amplitude limiter is designed so that most un-transduced sound is blocked out from reaching the middle ear by a highly effective sound absorbing material which is located within the ear piece. The earpiece has a thin-walled outer casing sized to provide an airtight fit inside the ear canal. Proper fit is achieved either by custom shaping each device for a particular wearer, or by providing an array of various shaped devices for a wearer to choose from.

U.S. Pat. No. 5,355,418 to Kelsey et al. discusses a frequency selective hearing protection device. When worn in the manner shown, this device performs a natural sound blocking function. It utilizes adaptive filtering to hinder the transmission of frequency components in ambient sound above a predetermined threshold. The device is encompassed in an ear unit fitting in the concha (outer ear) and having a plug portion partially inserted into the ear canal. The device must be appropriately sized for each wearer.

U.S. Pat. No. 5,305,387 to Sapiejewski discusses an earphone for use in an active noise reduction system. This earphone includes a shell accommodating a microphone closely adjacent to a driver shaped and sized to fit in the concha of an ear. A cushion is made of silicon gel covered by polyurethane film and is custom shaped for each wearer to provide comfort and a seal without moving the microphone away from the ear canal.

Embodiments are described in certain of the above references that employ earmuffs. However, the bulky size of earmuffs renders them inappropriate for many applications. For instance, earmuffs must seal the entire ear. Thick or long hairstyles can compromise the seal. Earmuffs can also interfere with the use of safety glasses or prescription glasses, protective gear, shields, gas masks, helmets, and cold weather clothing. Therefore, active noise reduction systems that mount within the wearer's ear are often preferable to earmuffs. However, inserting an audio device inside the ear canal raises safety and comfort issues analogous to those addressed by hearing aid designers. In that regard U.S. patent application Ser. No. 09/161,344, which is fully incorporated herein by reference, discloses a hearing device having a soft conformal tip that can be securely seated within the deep bony region of the ear canal, without causing appreciable pain or discomfort to the wearer.

Though active noise reduction systems mounted in the ear canal typically perform better than, for instance, systems mounted in earmuffs, a disadvantage of mounting such systems within the wearers ear is that conventional devices must each be custom fit to the individual wearer, increasing system cost.

For instance, U.S. Pat. No. 5,740,258 to Goodwin-Johansson discusses an active noise suppressor that fits in an ear canal without blocking the ear canal. The acoustically unobstructed passage allows the active reduction of undesired noise portions, while allowing the desired portions of the sound pressure waves to reach the eardrum. An integral housing is disclosed for securing the device inside the ear canal. The housing consists of elastic ribs attached to the circuit board, the ribs lodging the device in the ear canal.

U.S. Pat. No. 4,985,925 to Langberg et al. discloses an electronic earplug seated in the concha fossa (outer ear), which combines active and passive noise reduction in the quiet zone at the ear. The electronic earplug maintains an acoustical seal with a concha fossa and/or the external auditory meatus (ear canal). Noise that penetrates this passive barrier and reaches the quiet zone formed around the occluded ear canal volume adjacent the eardrum is further reduced by active means. However, neither Langberg et al. or Goodwin-Johansson address the problems of using "universal fit" devices for an in-the-ear-canal, active noise reduction system.

In particular, existing active noise reduction technology has several disadvantages. For instance, all the active noise reduction systems described above employ "feedback cancellation" systems to cancel unwanted noise. A problem associated with feedback cancellation systems is that they are prone to instability. Feedback systems tend to become unstable, for example, if the bandwidth of the system is too broad or the gain of the system is too high. When instability occurs, the system usually emits a loud noise that is generally unpleasant and occasionally dangerous. Consequently, the maximum range and effectiveness of feedback systems are limited by parameters designed to keep the feedback system stable.

To effect maximum cancellation, the waveform of the interacting anti-noise should exactly match the unwanted waveform, but should be inverted. The acoustic properties of each device, however, affect the characteristics of the anti-noise waveform. The effect of the acoustic properties may be corrected by processing the residual signal according to a transfer function characteristic of the acoustic properties of the system to compensate for the effects. However, these acoustic properties of the device are not constant under all conditions, and may vary with the force applied to the device in the wearer's ear. For example, when high pressure is applied to the device, or when the device is removed from the wearer's ear, the variation of the device's acoustic properties, particularly the volume and acoustic resistance, may cause instability in the feedback loop. This instability, in turn, causes the control loop to generate unstable oscillations, producing unpleasant and potentially even harmful noise.

In addition, many noise cancellation systems are designed not only to cancel unwanted noise, but also to provide particular sounds to the wearer. For example, earmuffs for listening to music or for use by pilots ideally cancel extraneous noise, and transmit particular desired sounds to the listener. Conventionally, the desired input signal is mixed with the residual signal from the internal microphone so that the desired signal is not canceled by the system. Feedback noise cancellation systems, however, because of their limited bandwidth, exhibit a high frequency rolloff having a relatively low cutoff frequency. Because of this cutoff frequency, higher frequencies of the desired sound tend to be attenuated, degrading the quality of the signal. Consequently, an equalizer must be added to return the sound to its proper amplitude.

In summary, noise-attenuating systems employing feedback noise cancellation have many disadvantages, including sensitivity to component location and unstability. Therefore, there is a need not only for an effective, low-cost, universal, in-the-ear-canal, active noise reduction system, but also for an active noise reduction system that does not exhibit the problems associated with feedback noise cancellation systems.

SUMMARY OF THE INVENTION

These needs and others are addressed by the noise attenuating devices and systems of the present invention. In a preferred embodiment, an earplug is provided having a replaceable soft tip, electronics with integrated multi-band automatic amplitude control, and active noise attenuation without feedback noise cancellation. The earplug preferably fits at least partially in the ear canal, and does not interfere with glasses, long hair, helmets, or cold weather clothing, etc. The earplug passively blocks sound waves having dangerous amplitudes and actively monitors incoming sound waves using a multi-channel automatic volume control circuit, passing through non-dangerous sound waves, and allowing the wearer to communicate in noisy environments. The earplug preferably avoids the cost of custom-fit devices by providing a universal earplug core comprising electronics along with a low-cost, disposable, universal soft tip to interface between the wearer's ear canal and the earplug core.

According to one aspect of the invention, a noise attenuating system in the earplug includes a core portion, comprising electronics and a housing. The electronics are adapted to attenuate unsafe amplitude sounds, and may comprise a microphone, circuitry, a speaker, and a battery. The circuitry receives a signal from the microphone, filters the signal into a plurality of bands, identifies each of the bands as corresponding either to a safe or unsafe amplitude sound, attenuates the unsafe amplitude sounds, and outputs to the speaker signals corresponding to safe amplitude sounds. The electronics thus actively filter sound, but do not provide active feedback cancellation. Instead of using feedback to cancel a sound wave, the system initially blocks all sound waves passively, then actively filters the sound waves, passing through sound waves of safe amplitude, such as speech sounds.

According to another aspect of the invention, the noise attenuating system further includes a deformable member, such as a disposable soft tip, adapted to fit at least partially inside a wearer's ear canal. In one embodiment, a universal deformable member has a hollow portion adapted to receive the core portion. The universal core portion can be inserted into the universal deformable member, and the assembly can be inserted at least partially into the ear canal. The core portion becomes removably engaged with the deformable member upon assembly. The deformable member holding the core portion deforms to the contour of the wearer's ear canal upon insertion, allowing the use of a universal core portion in a variety of differently shaped ear canals.

According to a further aspect of the invention, the electronics can comprise on/off switches, or switches facilitating the programming of the circuitry for different uses, such as switches for adjusting signal attenuation, frequency selection, and magnitude of noise suppression.

According to yet another aspect of the invention, the circuitry can be adapted to actively attenuate sound signals according to an active noise suppression algorithm. According to a still further aspect of the invention, an elongated flexible member is provided, such as a cord, which can be adapted to connect two earplugs. In one embodiment the elongated flexible member connects the core portions, while in another embodiment the elongated flexible member connects the deformable members. In yet other embodiments, the elongated flexible member connects either a core portion or a deformable member with another deformable member, such as a conventional earplug.

According to still another aspect of the invention, the elongated flexible member can comprise any or all of the electronics. For instance, the microphone can be attached to the elongated flexible member, and can be in communication with either one or two earplugs connected with the elongated flexible member. Likewise, all of the electronics can be attached with the elongated flexible member, as long as the sound waves output by the speaker are in communication with the interior of at least one ear canal.

Yet another aspect of the invention comprises adapting the noise attenuating electronics to earmuffs. Embodiments are provided for applications where earmuffs may be preferable to in-the-ear-canal devices, such as where the wearer already wears a hearing aid. Adding the active noise-filtering electronics of the present invention to otherwise conventional earmuffs allows wearers to hear safe amplitude sounds, which are broadcast by a speaker in the region between the earmuff and the ear, while avoiding unsafe amplitude sounds, which the earmuffs block through passive noise attenuation, and the electronics further attenuate. Another embodiment utilizes the same electronics module as the earplugs, such that the electronics module, or core portion, would be interchangeable between the earmuffs and the earplugs.

An additional aspect of the invention comprises adapting the noise attenuating electronics to a behind-the-ear device. In this embodiment, the noise attenuating electronics, other than the speaker, are located in a behind-the-ear housing similar to a behind-the-ear hearing aid device. The attenuated signal is sent via an electrical wire or other communication channel from the behind-the-ear device to a speaker mounted in a deformable member inside the ear canal. Embodiments positioning the housing in locations other than behind the ear are also contemplated in this aspect of the invention.

Other and further aspects and advantages of the invention will become apparent hereinafter.

BRIEF DESCRIPTION OF THE DRAWINGS

The drawings illustrate both the design and utility of the preferred embodiments of the present invention, in which similar elements in different embodiments are referred to by the same reference numbers for ease in illustrating the invention, wherein:

FIG. 10. is a front section view of a noise attenuating system constructed in accordance with an embodiment of the present invention.

FIG. 10a. is a left side view of the noise attenuating system of FIG. 10.

FIG. 11. is a front section view of a noise attenuating system constructed in accordance with an embodiment of the present invention.

FIG. 11a. is a left side view of the noise attenuating system of FIG. 11.

FIG. 12. is a front section view of a noise attenuating system constructed in accordance with an embodiment of the present invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided for illustration in order to fully convey the scope of the invention to those skilled in the art.

Figure 1:
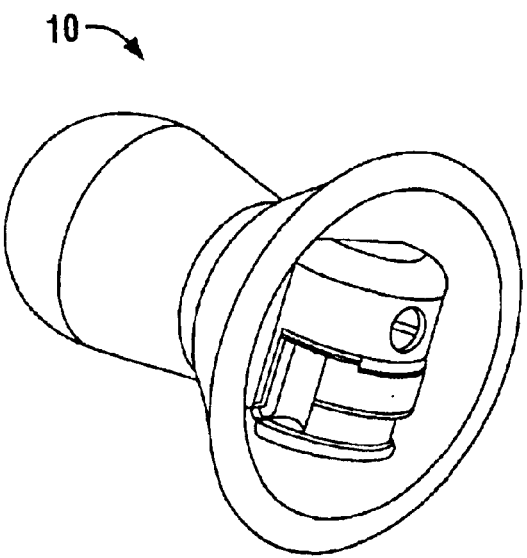
FIG. 1 is a front perspective view of a noise attenuating system constructed in accordance with an embodiment of the present invention.
Figure 2:
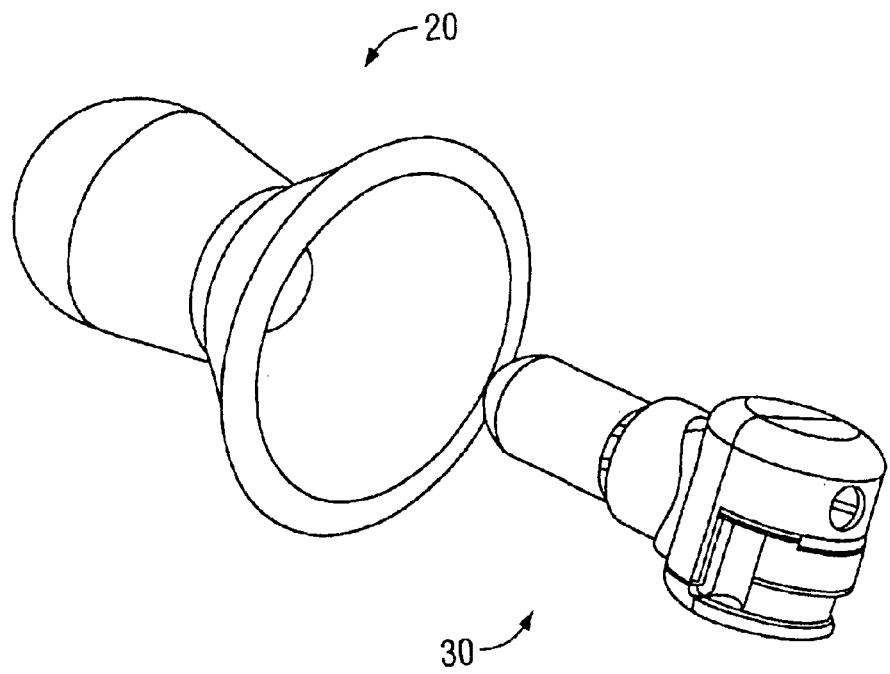
FIG. 2. is a front perspective view of the noise attenuating system of FIG. 1 with the deformable member separated from the core portion, both the deformable member and the core portion constructed in accordance with an embodiment of the present invention.
Figure 3:
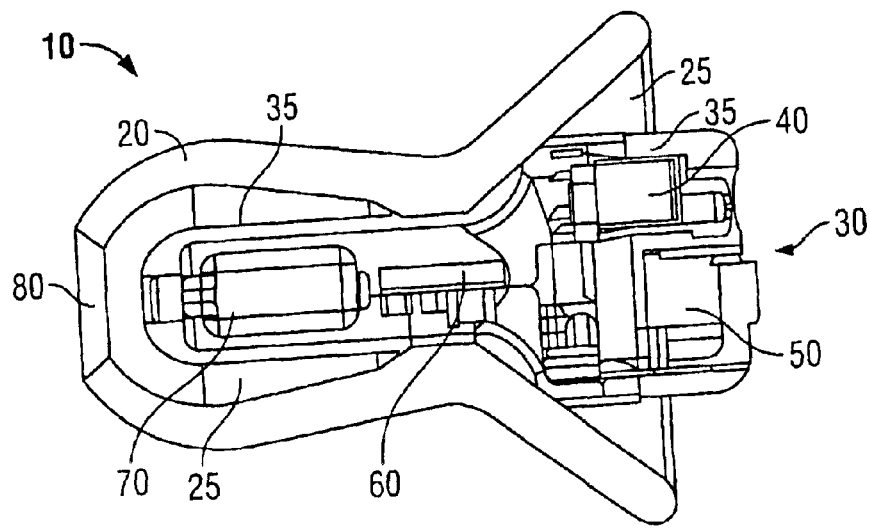
FIG. 3. is a cross sectional view of the noise attenuating system of FIG. 1.

A first embodiment of a noise attenuating system 10 according to the present invention is illustrated in FIG. 1. The noise attenuating system 10 includes a deformable member 20 and a core portion 30, shown separated in FIG. 2. A cross-sectional view of a first embodiment is illustrated in FIG. 3. In the embodiment shown in FIG. 3. a core portion 30 is assembled into a deformable member 20. The core portion 30 preferably is attached with a microphone 40, which is in electronic communication with electronic circuitry 60, the electronic circuitry 60 in electronic communication with a speaker 70. The microphone 40, electronic circuitry 60, and speaker 70 preferably receive electrical power originating from a battery 50. The battery 50 is preferably of the type used in hearing aids and is familiar to those skilled in the art. The deformable member 20 has an internal surface 25, the internal surface 25 preferably removably engaged with the external surface 35 of the core portion 30. The deformable member 20 preferably also has an opening 80 to allow sound waves to propagate from the speaker 70 to the inside of an ear canal (not shown). In a preferred embodiment, the deformable member 20 is constructed at least partially from an inexpensive, soft, resilient material, such as closed-cell foam rubber.

In normal operation, the noise attenuating system 10 is inserted at least partially into the ear canal of a wearer. The microphone 40, or other input transducer, is adapted to be located near the entrance of the ear canal and generates an electrical signal in response to sound pressure waves entering the wearer's ear. The electrical signal is communicated by conventional means, such as wires, from the microphone 40 to the electronic circuitry 60.

The noise attenuating system 10 is adapted to allow a wearer to hear safe amplitude sounds, such as normal speech and warnings, while protecting the wearer's hearing from unsafe amplitude sounds, such as loud machinery, explosions and the like. In one embodiment, this is accomplished first by passively blocking all sound waves from a wearer's ear canal by providing an airtight seal between the noise attenuating system 10 and the wearer's ear canal. Upon inserting the noise attenuating system 10 at least partially inside the wearer's ear canal, a portion of the deformable member 20 deforms to the match the contour of the wearer's ear canal, preferably removably engaging the noise attenuating system 10 inside the ear canal. In this manner, sound waves that would enter the wearer's ear canal in the absence of the noise attenuating system are physically blocked from entering the ear canal, providing passive noise attenuation, similar to a conventional earplug.

The noise attenuating system provides an improvement over conventional earplugs by providing a core portion 30 that is adapted to actively filter sound waves into various bands, passing only those frequency bands corresponding to safe amplitude sounds into the wearer's ear canal. The core portion 30 preferably has a hard shell external surface 35, such as injection-molded Nylon 6/6 plastic. Unlike conventional active noise cancellation systems, active noise attenuation is accomplished without providing additional sound waves inverse to unsafe amplitude sound waves. Instead, unsafe amplitude sound waves are passively blocked, and only safe amplitude sound waves are passed through to the wearer's ear canal. For instance, in one embodiment, the electronic circuitry 60 is adapted to: receive a signal from the microphone 40; filter the first signal into a plurality of bands; identify each of the bands as corresponding either to a safe amplitude sound or an unsafe amplitude sound; attenuate the amplitude of each of the bands that correspond to an unsafe amplitude sound; and to output to the speaker 70 a signal corresponding to a safe amplitude signal.

In a preferred embodiment, the electronic circuitry 60 comprises digital electronics, and is programmable for different uses. The electronic circuitry 60 may further include switches for adjusting signal attenuation, frequency selection, and magnitude of noise suppression. The electronic circuitry 60 preferably filters the electrical signal into a plurality of bands, preferably nine bands. Preferred embodiments of the electronic circuitry are disclosed and described in co-pending application Ser. No. 09/482,192, ("the '192 application") filed Jan. 12, 2000, entitled "Noise Reduction Apparatus and Method," which is fully incorporated herein by reference. In particular, a multi-band spectral subtraction scheme is disclosed in the '192 application, comprising a multi-band filter architecture, noise and signal power detection, and gain function for noise reduction.

In one embodiment, the noise reduction gain function comprises a gain scale function and a maximum attenuation function providing a predetermined amount of gain as a function of signal to noise ratio ("SNR") and noise. The gain scale function is a three-segment piecewise linear function, and the three piecewise linear sections of the gain scale function each include a first section providing maximum expansion up to a first knee point for maximum noise reduction, a second section providing less expansion up to a second knee point for less noise reduction, and a third section providing minimum or no expansion for input signals with high SNR to minimize distortion. Thus, three segments each comprising three sections are disclosed, for a total of nine bands.

The bands correspond to various sound wave frequencies entering the microphone 40. The electronic circuitry 60 evaluates the amplitudes of the various sound wave frequencies, and attenuates unsafe amplitude sound waves to safe amplitudes, including zero amplitude (i.e., complete cancellation). The electronic circuitry 60 then outputs an electrical signal to the speaker 70 via conventional means, such as wires. The electrical signal corresponds only to safe amplitude sounds that comprise either passed-through safe amplitude sounds or unsafe amplitude sounds attenuated to safe amplitudes.

The speaker 70 receives the electrical signal from the electronic circuitry 60 and converts the electrical signal to safe amplitude sound pressure waves corresponding to the electrical signal. The sound pressure waves leave the speaker 70 and travel past the deformable member 20, preferably through an opening 80 in the deformable member 20, and into the wearer's ear canal, toward the wearer's tympanic membrane (not shown). In this manner the noise attenuating system 10 passively blocks unsafe amplitude sounds from reaching the wearer's tympanic membrane, while actively forwarding safe amplitude sounds to the wearer's tympanic membrane.

In other embodiments the electronic circuitry 60 is adapted to actively attenuate sound signals according to an active noise suppression algorithm. In that regard, co-pending application Ser. No. 09/444,972, ("the '972 application"), filed Nov. 22, 1999, entitled "Hearing Aid Device Incorporating Signal Processing Techniques," which is fully incorporated herein by reference, discloses an active noise suppression algorithm incorporating multiplicative automatic gain control (AGC) circuits. The AGC circuits attenuate acoustic signals having a constant background level without removing the portions of the speech signal that contribute to intelligibility. The portion of the input signal that comprises the background noise portion of the acoustic signal is attenuated in amplitude without distortion to preserve the intelligibility of the acoustic input signal. The identification of the background noise portion of the acoustic signal is made by the constancy of the envelope of the input signal in each of the several frequency bands.

Turning to component shape, the noise attenuating system 10 is preferably shaped to comfortably fit inside most adults' ear canals to a depth sufficient to removably engage the noise attenuating system 10 inside the ear canal. The deformable member 20 and the core portion 30 are preferably shaped so that the deformable member 20 can deform to fit inside most adults' ear canals, while providing sufficient volume in the interior of the deformable member 20 to sufficiently house the core portion 30. The core portion 30 is preferably shaped to removably engage the deformable member, permitting easy and low cost replacement of the deformable member without replacing the core portion 30. In this manner, the noise attenuating system 10 of the present invention provides a universal active earplug that requires no expensive custom fitting for particular wearers.

Figure 4:
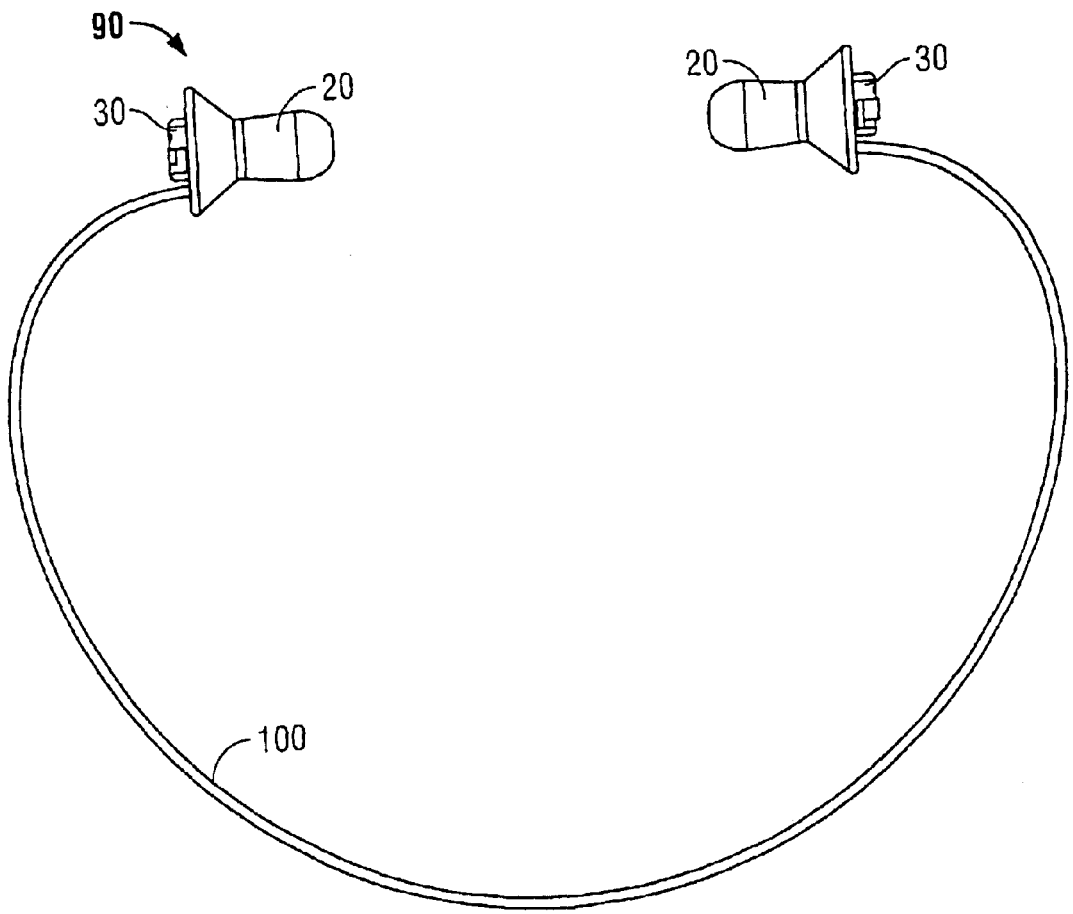
FIG. 4. is a front plan view of a noise attenuating system constructed in accordance with an embodiment of the present invention.
Figure 5:
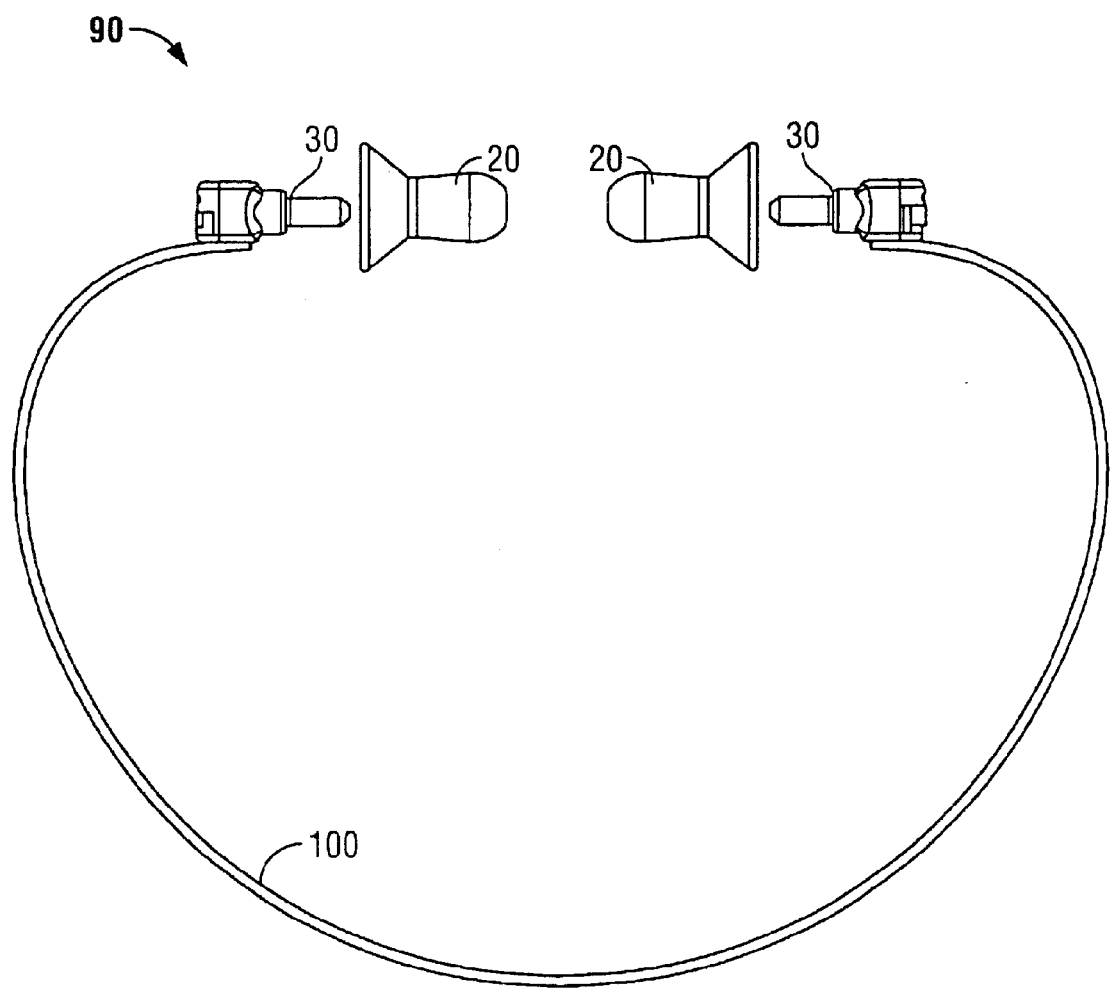
FIG. 5. is a front plan view of the noise attenuating system of FIG. 4 with the deformable members separated from the core portions, both the deformable members and the core portions constructed in accordance with an embodiment of the present invention.

A second noise attenuating system 90 of the present invention is illustrated in FIG. 4. In this embodiment, a cable 100 may join a first deformable member 20 and a first core portion 30 to a second deformable member 20 and a second core portion 30. The cable 100 may be attached either to a deformable member 20 or a core portion 30. Preferably the cable is attached to the first core portion 30 and the second core portion 30, as shown in FIG. 5. One purpose of the second embodiment 90 is to prevent component loss; if a first core portion should dislodge from a wearer's ear, the cable 100 will prevent the first core portion from falling to the ground and possibly being lost.

Figure 6:
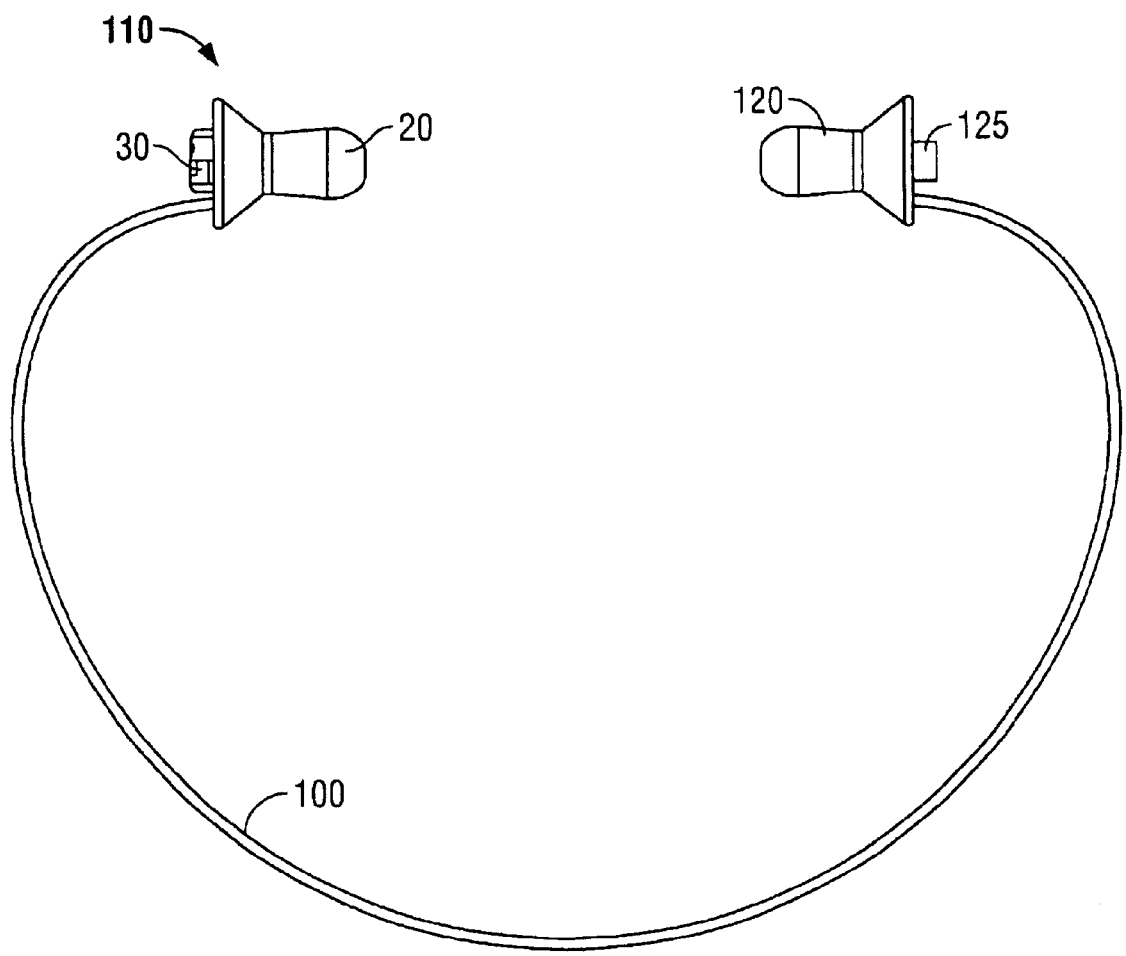
FIG. 6. is a front plan view of a noise attenuating system constructed in accordance with an embodiment of the present invention.

A third noise attenuating system 110 of the present invention is illustrated in FIG. 6. In this embodiment, a cable 100 may join a deformable member 20 and a core portion 30 to a conventional earplug 120. To prevent loss of the core portion 30, a first end of the cable is preferably attached to the core portion 30. Alternatively, a deformable member 20 can be substituted for the conventional earplug 120. The second end of the cable 100 can be attached either directly to the conventional earplug 120, or to a deformable member 20, or to a plug 125 adapted to removably engage a deformable member 20. One advantage of the system 110 is that only one core portion 30 need be provided, reducing overall system cost, while allowing the wearer to hear safe amplitude sounds with one ear.

Figure 7:
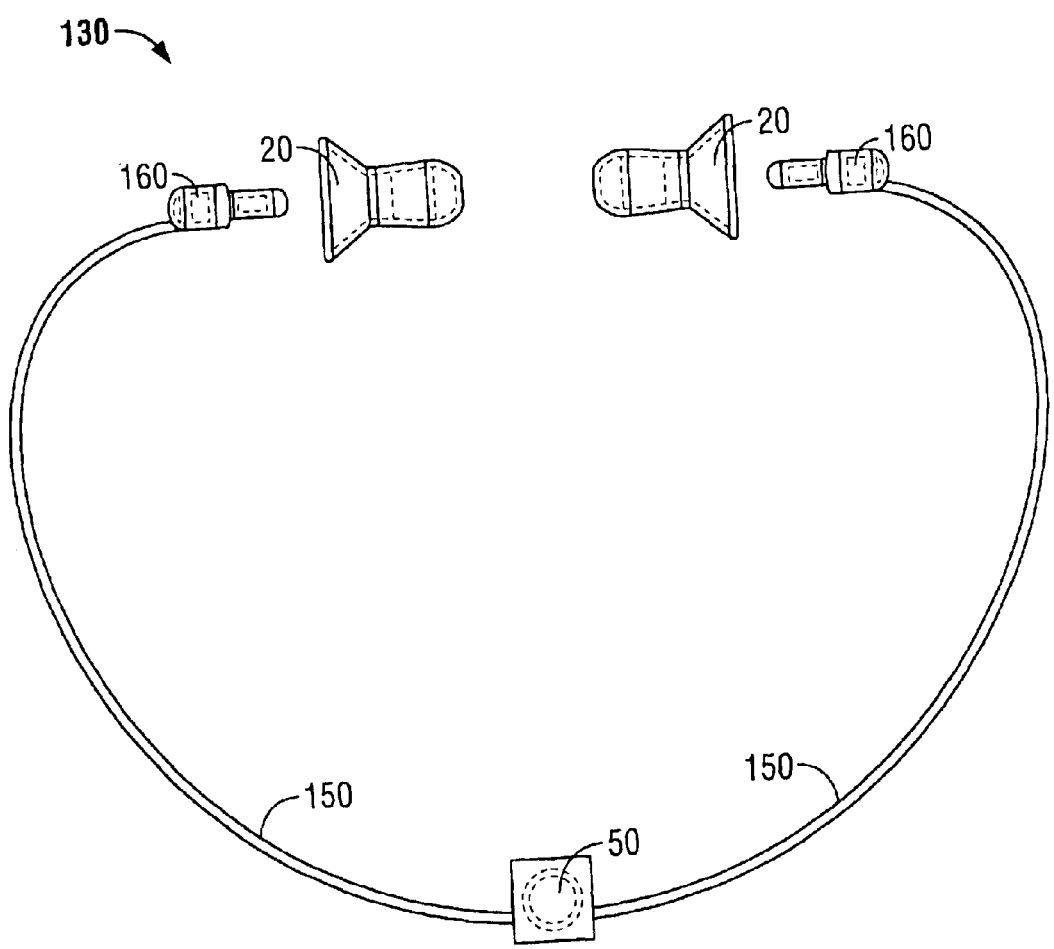
FIG. 7. is a front plan view of a noise attenuating system constructed in accordance with an embodiment of the present invention with the deformable members separated from the core portions, both the deformable members and the core portions constructed in accordance with an embodiment of the present invention.

A fourth noise attenuation system 130 of the present invention is illustrated in FIG. 7. In this embodiment, first and second deformable members 20 are adapted to removably engage first and second modified core portions 160, respectively. The modified core portions 160 are connected with first and second ends of a cable 150. A battery 50 is also connected with the cable 150. The modified core portions 160 contain all necessary electronic components other than the battery. The cable 150 comprises wires or other electronic communication means to allow power to flow from the battery 50 to the modified core portions 160. The system 130 advantageously reduces cost by replacing separate batteries 50 in each core section 30 with single battery 50 serving both ears.

Figure 8:
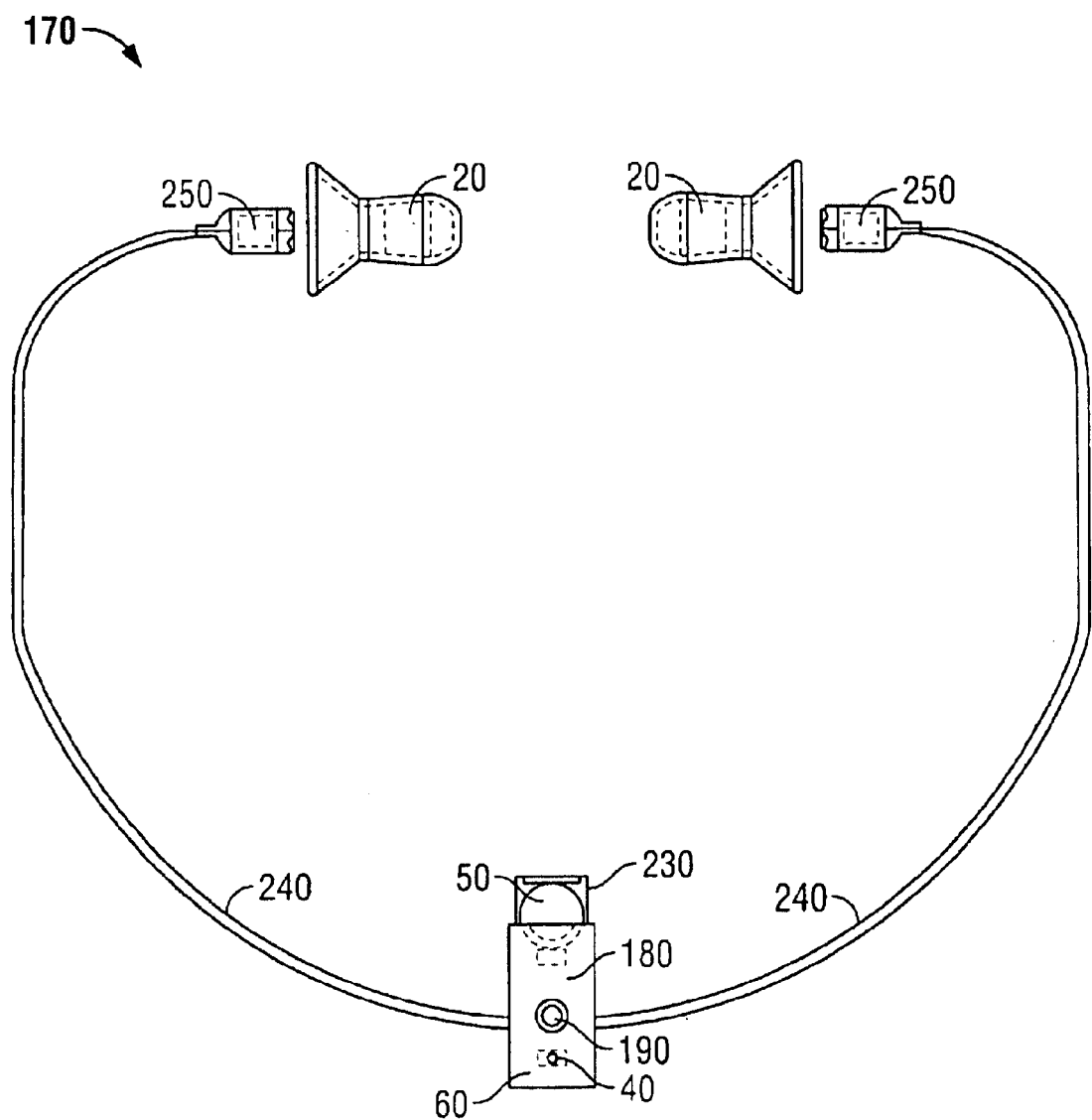
FIG. 8. is a front plan view of a noise attenuating system constructed in accordance with an embodiment of the present invention with the deformable members separated from the core portions, both the deformable members and the core portions constructed in accordance with an embodiment of the present invention.

A fifth noise attenuation 170 of the present invention is illustrated in FIG. 8. In this embodiment, first and second deformable members 20 are adapted to removably engage first and second modified core portions 250, respectively. The modified core portions 250 each comprise speakers 70 and are connected with first and second ends of a cable 240. Electronic components are also connected with the cable 240, such as a battery 50, battery door 230, housing 180, on/off switch 190, microphone 40, and electronic noise reduction circuitry 60. The cable 240 comprises wires, or other electronic communication means, to allow electrical signals to flow from the electronic noise reduction circuitry 60 to the speakers 70 in the modified core portions 250. The system 170 advantageously further reduces cost by replacing separate electrical components in each core section 30 with single electronic components that serve both ears.

Figure 9:
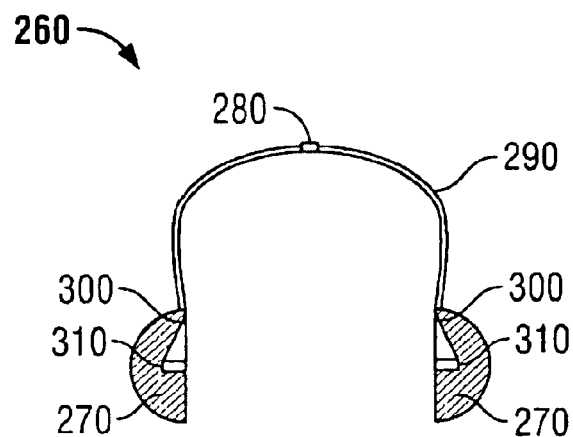
FIG. 9. is a front section view of a noise attenuating system constructed in accordance with an embodiment of the present invention.
Figure 9A:
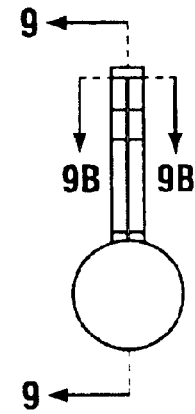
FIG. 9a. is a left side view of the noise attenuating system of FIG. 9.
Figure 9B:
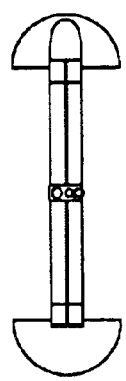
FIG. 9b. is a top section view of the noise attenuating system of FIG. 9.
Figure 9C:
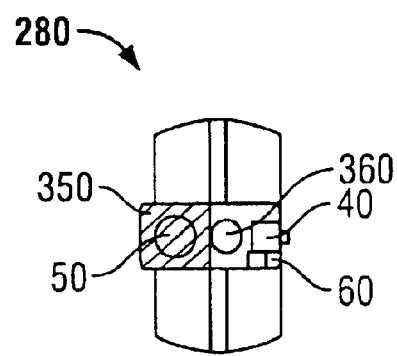
FIG. 9c. is top section view of the noise attenuating system of FIG. 9.

A sixth noise attenuation system 260 of the present invention is illustrated in FIG. 9. In this embodiment, noise attenuating earmuffs 270 are connected by a headband 290 and comprise speaker modules 310 and wires 300 to connect the speaker modules 310 to a microphone module 280. In a preferred embodiment the microphone module 280 is attached with the headband 290. As illustrated in FIG. 9c, the microphone module 280 comprises an on/off switch 360, a microphone 40, noise reduction electronic circuitry 60, a battery 50, and a battery door 350. The system 260 attenuates noise, while allowing the wearer to hear safe amplitude sound waves first by passively blocking all sound waves with the earmuffs 270, which are adapted to provide an airtight seal around the wearer's ears, as is well known in the art. Next, the electronic components function in the same fashion as the electronics in the above-described system 10 to produce electrical signals corresponding to safe amplitude sound waves. But unlike in the first system 10, where the electrical signals corresponding to safe amplitude sound waves are forwarded to a speaker 70, in system 260, the electrical signals corresponding to safe amplitude sound waves are forwarded over wires 300 to speaker modules 310, which are located in the earmuffs 270. The speaker modules 310 then receive the electrical signals forwarded by the electronic circuitry 60 over the wires 300 and convert the electrical signals to safe amplitude sound pressure waves corresponding to the electrical signals.

The sound pressure waves leave the speaker modules 310, which are adjacent the wearer's ear, and travel into the wearer's ear canal, toward the wearer's tympanic membrane (not shown). In this manner, the noise attenuating system 260 passively blocks unsafe amplitude sounds from reaching the wearer's tympanic membrane, while actively forwarding safe amplitude sounds to the wearer's tympanic membrane. An advantage of system 260 is that no device need penetrate the wearer's ear canal, thus this embodiment 260 can be utilized along with existing hearing aids, for instance.

Figure 10B:
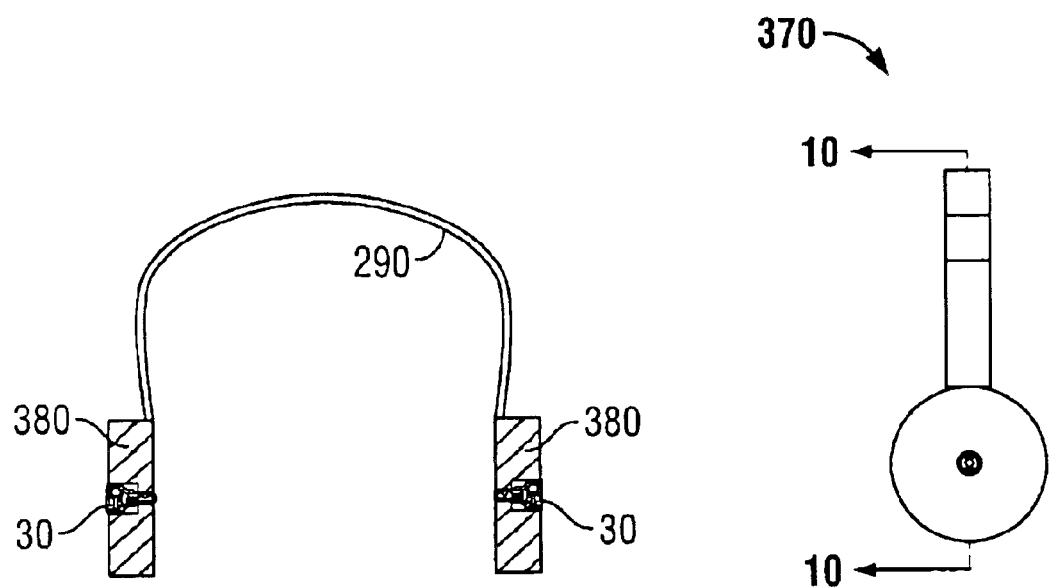
FIG. 10b. is a front section view of the noise attenuating system of FIG. 10.
Figure 10B:
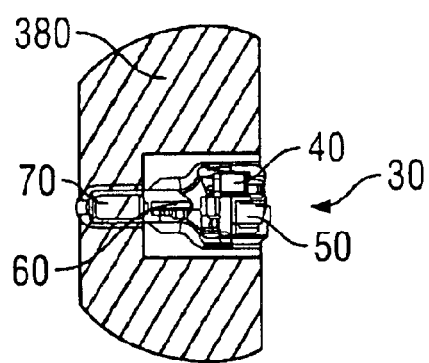

A seventh noise attenuation system 370 of the present invention is illustrated in FIG. 10. In this embodiment, noise attenuating earmuffs 380 are connected by a headband 290. The system 370 attenuates noise in the same fashion as system 260, with the exception that each earmuff 380 is adapted to accept the core portion 30 from the first embodiment 10. Like the above-described system 10, the core portion 30 in system 370 comprises a microphone 40, a battery 50, noise attenuating electronics 60, and a speaker 70, as illustrated in FIG. 10b. The system 370 employs the advantages of system 260, along with the further advantage of accepting standardized core portions 30.

An eighth noise attenuation system 390 of the present invention is illustrated in FIG. 11. In this embodiment, noise attenuating earmuffs 400 are connected by a headband 290. The system 390 attenuates noise in the same fashion as system 260, with the exception that separate electronics are located at each earmuff 400. Each earmuff 400 comprises a speaker module 410, a wire 420 connecting the speaker module 410 to a noise reduction electronic circuit 60, a microphone 40, and an on/off switch 460, as shown in FIG. 11a. A separate battery 50 can be located at each earmuff 400, or a single battery can be located elsewhere (not shown). Thus, system 390 provides improved sound quality to a wearer compared to system 260. Further, since each ear has its own audio signal, the wearer can determine the direction from which sounds emanate, which can be an important safety feature in dangerous environments.

A ninth noise attenuation system 470 of the present invention is illustrated in FIG. 12. This embodiment adapts the noise attenuating features of the present invention into what is known in the art as a "behind the ear" device. A modified deformable member 480 is adapted to be inserted in a wearer's ear canal and comprises earwax barriers 570 and a retrieval cord 580. The deformable member 480 is adapted to contain a speaker 550 in a speaker housing 560. The speaker 550 is electrically connected with one end of an electrical cable 500. The other end of the electrical cable 500 is electrically connected with electronic noise suppression circuitry 60, which is attached with a housing 490 adapted to be worn behind the ear. The housing 490 is also attached with a microphone 40, battery 50, and on/off switch 540. System 470 provides noise attenuation in the same manner as the first system 10, with the exception that some of the electronics are located in a housing 490 adapted to be worn behind the ear, instead of inside a core portion 30 adapted to be worn inside the ear.

Although the invention has been described and illustrated in the above descriptions and drawings, it will be understood that this description and these embodiments are by example only, and that numerous changes and modifications can be made by those skilled in the art without departing from the inventive concepts presented herein. Thus, the invention is not to be restricted, except by the following claims and their equivalents.

What is claimed is:

1. A noise attenuating system, comprising:
   a core portion, the core portion comprising electronics and a housing;
   the electronics adapted to attenuate unsafe amplitude sounds, the electronics comprising
      a microphone adapted to receive a first sound wave, and further adapted to output a first signal corresponding to the first sound wave;
      circuitry adapted to
         receive the first signal,
         filter the first signal into a plurality of bands,
         identify each of the bands as corresponding to either a first safe amplitude sound or an unsafe amplitude sound,
         attenuate the amplitude of each of the bands that correspond to an unsafe amplitude sound, and
         output a second signal, the second signal corresponding to a second safe amplitude sound;
      a speaker adapted to receive the second signal, and further adapted to output a second sound wave corresponding to the second signal;
   the housing comprising a first body;
   a deformable member adapted to fit at least partially inside an ear canal, the deformable member comprising a second body, the second body having an external surface and an internal surface defining an interior portion;
   wherein the core portion is adapted to fit at least partially inside the interior portion of the deformable member.

2. The noise attenuating system of claim 1, wherein the electronics further comprise a battery.

3. The noise attenuating system of claim 1, wherein the electronics further comprise a first switch, the first switch comprising a first setting and a second setting, wherein the first switch is adapted to enable the circuitry.

4. The noise attenuating system of claim 1, wherein the deformable member is adapted to be disposable.

5. The noise attenuating system of claim 1, wherein the core portion is adapted to be reusable.

6. The noise attenuating system of claim 1, wherein the external surface of the deformable member is adapted to removably engage an ear canal.

7. The noise attenuating system of claim 1, wherein the core portion is adapted to removably engage the internal surface of the deformable member.

8. The noise attenuating system of claim 1, wherein the first safe amplitude sound is a normal speech sound.

9. The noise attenuating system of claim 1, wherein the circuitry is further adapted to actively attenuate sound signals according to an active noise suppression algorithm.

10. The noise attenuating system of claim 1, wherein the electronics further comprise a switch adapted to control attenuation levels of the plurality of bands.

11. A noise attenuating system, comprising:
   a first core portion comprising a first body defining a first housing;
   a second core portion comprising a second body defining a second housing;
   an elongated flexible member comprising a third body with a proximal end and a distal end;
   wherein the first core portion is attached to the proximal end of the elongated flexible member, and the second core portion is attached to distal end of the elongated flexible member;
   wherein the first core portion, the second core portion, and the elongated flexible member collectively comprise electronics adapted to attenuate unsafe amplitude sounds, the electronics comprising
      a microphone adapted to receive a first sound wave, and further adapted to output a first signal, the first signal corresponding to the first sound wave;
      circuitry adapted to
         receive the first signal,
         filter the first signal into a plurality of bands,
         identify each of the bands as corresponding to either a first safe amplitude sound or an unsafe amplitude sound,
         attenuate the amplitude of each of the bands that correspond to an unsafe amplitude sound, and
         output a second signal, the second signal corresponding to a second safe amplitude sound;
      a speaker adapted to receive the second signal, and further adapted to output a second sound wave corresponding to the second signal.
   a first deformable member adapted to fit at least partially inside a first ear canal, the first deformable member comprising a fourth body, the fourth body having a first external surface and a first internal surface defining a first interior portion;
   a second deformable member adapted to fit at least partially inside a second ear canal, the second deformable member comprising a fifth body having a second external surface and a second internal surface defining a second interior portion;
   wherein the first core portion is adapted to fit at least partially inside the first interior portion of the first deformable member; and
   wherein the second core portion is adapted to fit at least partially inside the second interior portion of the second deformable member.

12. The noise attenuating system according to claim 1, wherein the microphone is attached with the elongated flexible member.

13. A noise attenuating system, comprising:
   a core portion comprising a first body defining a housing;
   a first deformable member adapted to fit at least partially inside a first ear canal, the first deformable member comprising a second body having a first external surface;
   an elongated flexible member comprising a third body with a proximal end and a distal end;

wherein the core portion is attached to the proximal end of the elongated flexible member, and the first deformable member is attached to distal end of the elongated flexible member;

wherein the first core portion, the first deformable member, and the elongated flexible member collectively comprise electronics adapted to attenuate unsafe amplitude sounds, the electronics comprising a microphone adapted to receive a first sound wave, and further adapted to output a first signal corresponding to the first sound wave;

circuitry adapted to
receive the first signal,
filter the first signal into a plurality of bands,
identify each of the bands as corresponding to either a first safe amplitude sound or an unsafe amplitude sound,
attenuate the amplitude of each of the bands that correspond to an unsafe amplitude sound, and
output a second signal corresponding to a second safe amplitude sound;

a speaker adapted to receive the second signal, and further adapted to output a second sound wave corresponding to the second signal.

a second deformable member adapted to fit at least partially inside a second ear canal, the second deformable member comprising a fourth body, the fourth body having a second external surface and an internal surface defining an interior portion;

wherein the core portion is adapted to fit at least partially inside the interior portion of the second deformable member.

14. The noise attenuating system according to claim 13, wherein the microphone is attached with the elongated flexible member.

15. Electronics for use in a noise attenuating system, comprising:

a microphone adapted to receive a first sound wave, and further adapted to output a first signal corresponding to the first sound wave;

circuitry adapted to
receive the first signal,
filter the first signal into a plurality of bands,
identify each of the bands as corresponding to either a first safe amplitude sound or an unsafe amplitude sound, attenuate the amplitude of each of the bands that correspond to an unsafe amplitude sound, and
output a second signal corresponding to a second safe amplitude sound;

a speaker adapted to receive the second signal, and further adapted to output a second sound wave corresponding to the second signal.

16. A noise attenuating earmuff assembly, comprising:

a first sound-insulating cup adapted to cover and provide a seal over a first ear, creating a first sealed area between the first sound-insulating cup and the first ear;

a second sound-insulating cup adapted to cover and provide a seal over a second ear, creating a second sealed area between the second sound-insulating cup and the second ear;

a headband comprising an elongated body having a first end and a second end, the first end of the headband connected to the first sound-insulating cup, and the second end of the headband connected to the second sound insulating cup, the headband is adapted to position the first sound-insulating cup over the first ear and the second sound-insulating cup over the second ear;

electronics adapted to attenuate unsafe amplitude sounds, the electronics comprising a microphone adapted to receive a first sound wave, and further adapted to output a first signal corresponding to the first sound wave;

circuitry adapted to:
receive the first signal,
filter the first signal into a plurality of bands,
identify each of the bands as corresponding to either a first safe amplitude sound or an unsafe amplitude sound,
attenuate the amplitude of each of the bands that correspond to an unsafe amplitude sound, and
output a second signal corresponding to a second safe amplitude sound;

a speaker adapted to receive the second signal, and further adapted to output a second sound wave corresponding to the second signal;

wherein the speaker is either
attached to the first sound-insulating cup and is adapted to output the second sound wave into the first sealed area between the first sound-insulating cup and the first ear, or
attached to the second sound-insulating cup and is adapted to output the second sound wave into the second sealed area between the second sound-insulating cup and the second ear.

17. A noise attenuating system, comprising:

an outside-the-ear portion comprising a housing and electronics attached with the housing, the electronics adapted to attenuate unsafe amplitude sounds, the electronics comprising a microphone adapted to receive a first sound wave, and further adapted to output a first signal corresponding to the first sound wave, circuitry adapted to
receive the first signal,
filter the first signal into a plurality of bands,
identify each of the bands as corresponding to either a first safe amplitude sound or an unsafe amplitude sound,
attenuate the amplitude of each of the bands that correspond to an unsafe amplitude sound, and
output a second signal, the second signal corresponding to a second safe amplitude sound;

the housing adapted to be worn by a wearer on the outside of the wearer's ear;

an electrical communication path adapted to electrically connect the circuitry with a speaker, the speaker located remote from the housing, the speaker adapted to receive the second signal, and further adapted to output a second sound wave corresponding to the second signal; and a deformable member adapted to fit at least partially inside an ear canal, the deformable member comprising a body having an external surface and an internal surface defining an interior portion;

wherein the speaker is adapted to fit at least partially inside the interior portion of the deformable member.

* * * * *